US00PP24306P2

(12) United States Plant Patent
Dümmen

(10) Patent No.: US PP24,306 P2
(45) Date of Patent: Mar. 11, 2014

(54) ***BEGONIA* PLANT NAMED 'BBFLARO'**

(50) Latin Name: *Begonia×hiemalis*
Varietal Denomination: BBFLARO

(75) Inventor: Tobias Gunter Dümmen, Rheinberg (DE)

(73) Assignee: Begonia Breeders Association B.V., Rijsenhout (NL)

( * ) Notice: Subject to any disclaimer, the term of this patent is extended or adjusted under 35 U.S.C. 154(b) by 20 days.

(21) Appl. No.: 13/507,524

(22) Filed: Jul. 5, 2012

(51) Int. Cl.
*A01H 5/00* (2006.01)

(52) U.S. Cl.
USPC ..... Plt./348

(58) Field of Classification Search
USPC ..... Plt./348
See application file for complete search history.

*Primary Examiner* — Kent L Bell
(74) *Attorney, Agent, or Firm* — C. A. Whealy

(57) ABSTRACT

A new and distinct cultivar of *Begonia* plant named 'BBFLARO', characterized by its compact, upright and mounded plant habit; freely branching habit; numerous double flowers that are dark pink in color; and good postproduction longevity.

1 Drawing Sheet

Botanical designation: *Begonia×hiemalis.*
Cultivar denomination: 'BBFLARO'.

BACKGROUND OF THE INVENTION

The present invention relates to a new and distinct cultivar of *Begonia* plant, botanically known as *Begonia×hiemalis*, commercially known as Elatior *Begonia* and hereinafter referred to by the name 'BBFLARO'.

The new *Begonia* plant is a product of a planned breeding program conducted by the Inventor in Aalsmeer, The Netherlands. The objective of the breeding program is to develop new freely branching *Begonia* plants with attractive flower color.

The new *Begonia* plant originated from a cross-pollination made by the Inventor during the summer of 2008 of a proprietary selection of *Begonia×hiemalis* identified as code number 2011241-3, not patented, as the female, or seed, parent with an unnamed selection of *Begonia socotrana*, not patented, as the male, or pollen, parent. The new *Begonia* plant was discovered and selected by the Inventor as a single flowering plant from within the progeny of the stated cross-pollination in a controlled greenhouse environment in Aalsmeer, The Netherlands in May, 2010.

Asexual reproduction of the new *Begonia* plant by terminal cuttings in a controlled greenhouse environment in Aalsmeer, the Netherlands since the autumn of 2010 has shown that the unique features of this new *Begonia* plant are stable and reproduced true to type in successive generations.

SUMMARY OF THE INVENTION

Plants of the new *Begonia* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'BBFLARO'.

These characteristics in combination distinguish 'BBFLARO' as a new and distinct *Begonia* plant:

1. Compact, upright and mounded plant habit.
2. Freely branching habit.
3. Numerous double flowers that are dark pink in color.
4. Good postproduction longevity.

Plants of the new *Begonia* differ primarily from plants of the female parent selection in branching habit as plants of the new *Begonia* are more freely branching than plants of the female parent selection.

Plants of the new *Begonia* differ primarily from plants of the male parent selection in flower form as plants of the new *Begonia* have double flowers whereas plants of the male parent selection have single flowers.

Plants of the new *Begonia* can be compared to plants of *Begonia×hiemalis* 'BBDRA', disclosed in U.S. Plant Pat. No. 19,700. In side-by-side comparisons conducted in Aalsmeer, The Netherlands, plants of the new *Begonia* differed primarily from plants of 'BBDRA' in the following characteristics:

1. Plants of the new *Begonia* were more compact than plants of 'BBDRA'.
2. Flowers of plants of the new *Begonia* had more tepals than flowers of plants of 'BBDRA'.
3. Plants of the new *Begonia* and 'BBDRA' differed in flower color as flowers of plants of 'BBDRA' were light red in color.

BRIEF DESCRIPTION OF THE PHOTOGRAPH

The accompanying colored photograph illustrates the overall appearance of the new *Begonia* plant showing the colors as true as it is reasonably possible to obtain in colored reproductions of this type. Colors in the photograph may differ slightly from the color values cited in the detailed botanical description which accurately describe the colors of the new *Begonia* plant. The photograph comprises a side perspective view of a typical flowering plant of 'BBFLARO' grown in a container.

DETAILED BOTANICAL DESCRIPTION

Plants used for the aforementioned photograph and following observations and measurements were grown during the spring and summer in 13-cm containers in a shaded glass-covered greenhouse in Aalsmeer, The Netherlands and grown under typical *Begonia* production practices. During the production of the plants day and night temperatures ranged from 15° C. to 20° C. and maximum light levels were 18,000 lux. Plants were 15 weeks old when the photograph and description were taken. In the following description, color references are made to The Royal Horticultural Society Colour Chart, 2001 Edition, except where general terms of ordinary dictionary significance are used.

Botanical classification: *Begonia×hiemalis* 'BBFLARO'.

Commercial classification: Elatior *Begonia*.

Parentage:

*Female, or seed, parent*.—Proprietary selection of *Begonia×hiemalis* identified as code number 2011241-3, not patented.

*Male, or pollen, parent*.—Unnamed selection of *Begonia socotrana*, not patented.

Propagation:

*Type*.—By terminal vegetative cuttings.

*Time to initiate roots*.—About 15 days at temperatures of 20° C.

*Time to produce a rooted young plant*.—About 14 to 18 days at temperatures of 20° C.

*Root description*.—Medium in thickness, fibrous, white in color; plants of the new *Begonia* have not been observed to form tubers.

*Rooting habit*.—Freely branching; medium density.

Plant description:

*Plant form*.—Compact, upright and mounded plant habit, inverted triangle; freely branching with good stem and stem base strength; flowers are fully double and abundant; moderately vigorous growth habit.

*Plant height*.—About 20 cm to 25 cm.

*Plant width*.—About 25 cm to 30 cm.

*Basal branch description*.—Quantity: Freely basal branching with about five to six basal branches developing per plant. Length: About 9 cm to 13 cm. Diameter: About 1 cm to 3 cm. Texture: Smooth, glabrous. Color: Close to 144B.

*Leaf description*.—Arrangement: Simple, alternate. Length: About 8 cm to 9 cm. Width: About 5 cm to 6 cm. Shape: Roughly deltoid. Apex: Acute to acuminate. Base: Cordate to oblique. Margin: Dentate to serrate. Texture, upper surface: Smooth, glabrous; velvety. Texture, lower surface: Pubescent. Venation pattern: Palmate. Color: Developing and fully expanded leaves, upper surface: Close to 132A; venation, close to 138A. Developing and fully expanded leaves, lower surface: Close to 132B; venation, close to 138A. Petiole length: About 4 cm to 6 cm. Petiole diameter: About 4 mm. Petiole texture, upper and lower surfaces: Smooth, glabrous. Petiole color, upper and lower surfaces: Close to 138B.

Flower description:

*Flowering habit*.—Double flowers with numerous tepals arranged in axillary cymes; typically four to six open flowers per cyme; many cymes in flower simultaneously; flowers positioned upright and outwardly above the foliar plane.

*Fragrance*.—None detected.

*Natural flowering season*.—Plants will flower continuously year round in the greenhouse, however plants flower earlier and more abundantly during the summer in The Netherlands.

*Postproduction longevity*.—Good postproduction longevity, flowers last about four to five weeks on the plant; flowers persistent.

*Cyme height*.—About 6 cm to 8 cm.

*Cyme diameter*.—About 6 cm to 7 cm.

*Flowers*.—Shape: Oval; rose-like. Length: About 4 cm to 5 cm. Diameter: About 4 cm to 6 cm. Depth: About 1 cm to 2 cm.

*Flower buds*.—Length: About 2 cm. Diameter: About 2 cm. Shape: Oval. Color: Close to 72D.

*Tepals*.—Arrangement: Rosette. Quantity: About 15 to 20 per flower. Length: About 2 cm to 3 cm. Width: About 3 cm to 4 cm. Shape: Obovate. Apex: Rounded, obtuse. Base: Cordate. Margin: Entire, undulate. Texture, upper and lower surfaces: Smooth, glabrous; satiny. Color: When opening and fully opened, upper surface: Close to 72D. When opening and fully opened, lower surface: Close to 72D.

*Flower bracts*.—Quantity/arrangement: Two, opposite. Shape: Broadly ovate. Apex: Obtuse. Margin: Entire. Texture, upper and lower surfaces: Smooth, glabrous. Color, upper and lower surfaces: Close to 144B overlain with close to 183A.

*Peduncles*.—Length: About 4 cm to 5 cm. Diameter: About 3 mm to 4 mm. Angle: About 30° to 45° from vertical. Strength: Strong. Texture: Smooth, glabrous. Color: Close to 144B.

*Pedicels*.—Length: About 2 cm to 3 cm. Diameter: About 2 mm to 3 mm. Angle: About 30° to 45° from the peduncle. Strength: Strong. Texture: Smooth, glabrous. Color: Reddish green.

*Reproductive organs*.—Stamens: None observed. Pistils: None observed.

*Seeds and fruits*.—Seed and fruit development have not been observed on plants of the new *Begonia*.

Disease & pest resistance: Resistance to pathogens and pests common to *Begonia* has not been observed on plants of the new *Begonia*.

Temperature tolerance: Plants of the new *Begonia* have been observed to tolerate temperatures from about 10° C. to about 35° C.

It is claimed:

1. A new and distinct *Begonia* plant named 'BBFLARO' as illustrated and described.

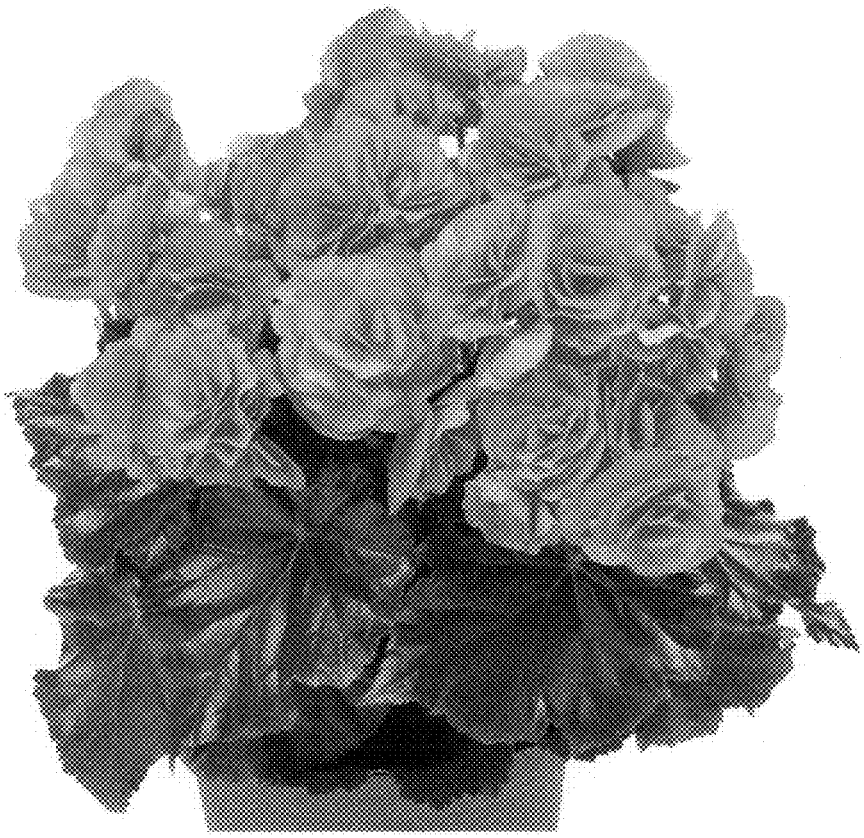

* * * * *